(12) United States Patent
Fourroux

(10) Patent No.: US 11,628,073 B2
(45) Date of Patent: Apr. 18, 2023

(54) WALKING CANISTER SYSTEM AND DEVICE FOR AMPUTEE SOCKET MANUFACTURE AND ASSOCIATED METHODS

(71) Applicant: Marvin R. Fourroux, Orange Beach, AL (US)

(72) Inventor: Marvin R. Fourroux, Orange Beach, AL (US)

( * ) Notice: Subject to any disclaimer, the term of this patent is extended or adjusted under 35 U.S.C. 154(b) by 174 days.

(21) Appl. No.: 16/943,667

(22) Filed: Jul. 30, 2020

(65) Prior Publication Data

US 2021/0315717 A1    Oct. 14, 2021

Related U.S. Application Data

(60) Provisional application No. 63/006,887, filed on Apr. 8, 2020.

(51) Int. Cl.
| | |
|---|---|
| *A61F 2/80* | (2006.01) |
| *A61F 2/78* | (2006.01) |
| *A61F 2/50* | (2006.01) |

(52) U.S. Cl.
CPC .............. *A61F 2/80* (2013.01); *A61F 2/7812* (2013.01); *A61F 2/5044* (2013.01); *A61F 2002/7818* (2013.01); *A61F 2002/802* (2013.01)

(58) Field of Classification Search
CPC .... A61F 2/80; A61F 2002/807; A61F 2/7812; A61F 13/0223; A61F 2013/53769; A61F 2/78; A61F 2002/802
See application file for complete search history.

(56) References Cited

U.S. PATENT DOCUMENTS 5,549,709 A  *  8/1996  Caspers ................... A61F 2/80
                                                     623/24

* cited by examiner

*Primary Examiner* — Stella K Yi

(74) *Attorney, Agent, or Firm* — Collaborative IP; Paul Ditmyer

(57) ABSTRACT

The walking canister system and method are for manufacturing a prosthetic socket. The system includes a rigid canister, a suspension bladder positioned within the rigid canister, and an outer chamber wicking material arranged in an outer chamber defined between the suspension bladder and the rigid canister. A foam insert includes a contoured exterior surface configured to transfer pressure through to an interior surface thereof to produce consistent surface contact with a residual limb, of a walking patient, having casting material thereon. An inner chamber wicking material is arranged in an inner chamber defined between the foam insert and the suspension bladder. An outer chamber vacuum port is in fluid communication with the outer chamber, and an inner chamber vacuum port is in fluid communication with the inner chamber. An outer chamber suspension sleeve is configured to extend from the residual limb and over the rigid canister.

14 Claims, 11 Drawing Sheets

US 11,628,073 B2

WALKING CANISTER SYSTEM AND DEVICE FOR AMPUTEE SOCKET MANUFACTURE AND ASSOCIATED METHODS

RELATED APPLICATIONS

This application claims priority to U.S. Provisional Application Ser. No. 63/006,887 filed Apr. 8, 2020 titled "WALKING CANISTER SYSTEM AND DEVICE FOR AMPUTEE SOCKET MANUFACTURE AND ASSOCIATED METHODS" which is incorporated herein in its entirety by reference.

FIELD OF THE INVENTION

The present invention relates in general to the medical field, and in particular to prosthetic devices and associated methods.

BACKGROUND OF THE INVENTION

In general, various current techniques involve modeling or measuring an amputee's residual limb (e.g. above the knee or below the knee) via casting or digitization while the patient is in a static position (e.g. a sitting position), which provides a static model. In other words, by casting or digitizing in a sitting/static position, a static model is the result. When such a prosthetic socket is created in a static model, undue pressure and skin breakdown problems are produced on the boney anatomy of the residuum, primarily the anterior distal end of the tibia and the fibula head. It should be clear that the orientation of the boney anatomy is not in the optimal or correct position in the current socket model approach.

Other techniques include U.S. Pat. No. 5,503,543 to Laghi which is directed to a prosthetic casting machine that receives an amputated stump while a patient is standing so that a hard socket can be made based upon the shape of the stump when it is under load. The patient's stump is inserted into a liner and the liner is coated with plaster before the stump is inserted into the machine. After insertion, while the patient is standing, compressed air is introduced into a space between a transparent flexible bladder and a transparent rigid cylinder so that a pressure is applied to the plaster by the bladder.

However, it may be desirable to measure an amputee's residual limb by capturing the shape in motion to provide an accurate fit, increased comfort in the socket, less harm to the patients limb, and more accurate alignment of the relationship between the socket and the foot. If the patient is measured while upright and/or walking, a more dynamic measurement will be captured. By capturing the shape in motion, it takes all three planes into consideration; sagittal, frontal, transverse. Humans are tri-planer beings, so the most accurate measurement and fit is when patient is using all three planes.

This background section is intended to introduce the reader to various aspects of typical technology that may be related to various aspects or embodiments of the present invention, which are described and/or claimed below. This discussion is believed to be useful in providing the reader with background information to facilitate a better understanding of the various aspects and embodiments of the present invention. Accordingly, it should be understood that these statements are to be read in light of, and not as admissions of, the prior art.

SUMMARY OF THE INVENTION

It is an object of the present embodiments to provide a system, device and method to measure an amputee's residual limb by capturing the shape thereof in motion to provide an accurate fit, increased comfort in the socket, less harm to the patients limb, and more accurate alignment of the relationship between the socket and the foot.

This and other objects, advantages and features in accordance with the present embodiments may be provided by a walking canister system for manufacturing a prosthetic socket. The system includes a rigid canister including an open end at a top, a suspension bladder positioned within the rigid canister, and an outer chamber wicking material arranged in an outer chamber defined between the suspension bladder and the rigid canister. A foam insert is positioned within the suspension bladder and including a contoured exterior surface configured to transfer pressure through to an interior surface thereof to produce consistent surface contact with a residual limb, of a walking patient, having casting material thereon. An inner chamber wicking material is arranged in an inner chamber defined between the foam insert and the suspension bladder. An outer chamber vacuum port is positioned in the rigid canister and in fluid communication with the outer chamber, and an inner chamber vacuum port is positioned in the rigid canister and in fluid communication with the inner chamber. An outer chamber suspension sleeve is configured to extend from the residual limb and over the rigid canister.

Additionally, and/or alternatively, a pylon attachment is located at the bottom of the rigid canister and includes a channel in fluid communication with the inner chamber vacuum port. The inner chamber vacuum port may be defined by an interlocking plate at the bottom of the rigid canister.

Additionally, and/or alternatively, a pylon is attached to the pylon attachment, and a floor interface member positioned at a bottom of the pylon and configured to provide consistent pressure upward through the pylon to the rigid canister during a casting-walking process.

Additionally, and/or alternatively, the rigid canister comprises a thermoplastic rigid canister.

Additionally, and/or alternatively, the contoured exterior surface of the foam insert comprises a waffle pattern defining a contoured pattern of squares. The foam insert may be a compressible foam material including urethane and/or silicon flexible foam.

Other objects, advantages and features in accordance with the present embodiments may be provided by a walking canister method for manufacturing a prosthetic socket. The method includes providing a rigid canister including an open end at the top, and positioning a suspension bladder within the rigid canister along with an outer chamber wicking material arranged in an outer chamber defined between the suspension bladder and the rigid canister. Th method further includes positioning a foam insert within the suspension bladder and including a contoured exterior surface configured to transfer pressure through to an interior surface thereof to produce consistent surface contact with a residual limb, of a walking patient, having casting material thereon. An inner chamber wicking material is arranged in an inner chamber defined between the foam insert and the suspension bladder. The method includes forming an outer chamber vacuum port in the rigid canister and in fluid communication with the outer chamber, and forming an inner chamber vacuum port in the rigid canister and in fluid communication with the inner chamber. An outer chamber suspension sleeve is extended around the top of the rigid canister.

Additionally, and/or alternatively, the method incudes connecting a pylon attachment at the bottom of the rigid canister and including a channel in fluid communication with the inner chamber vacuum port. The inner chamber vacuum port may be defined by an interlocking plate at the bottom of the rigid canister.

Additionally, and/or alternatively, the method includes attaching a pylon to the pylon attachment, and positioning a floor interface member at a bottom of the pylon and configured to provide consistent pressure upward through the pylon to the rigid canister during a casting-walking process.

Additionally, and/or alternatively, the method includes applying suction to the outer chamber vacuum port and the inner chamber vacuum port to adjust pressure within the outer chamber and the inner chamber.

Additionally, and/or alternatively, the contoured exterior surface of the foam insert comprises a waffle pattern defining a contoured pattern of squares.

Additionally, and/or alternatively, the foam insert comprises a compressible foam material including at least one of urethane and silicon flexible foam.

Other objects, advantages and features in accordance with the present embodiments may be provided by a foam insert for use in manufacturing a prosthetic socket. The foam insert includes an elongated foam body extending from an open end to a closed end, and configured to be positioned within a rigid canister. The elongated foam body includes a contoured exterior surface configured to transfer pressure through to an interior surface thereof to produce consistent surface contact with a residual limb having casting material thereon.

Additionally, and/or alternatively, the contoured exterior surface of the foam insert comprises a waffle pattern defining a contoured pattern of squares. The contoured exterior surface of the foam insert may comprise a matrix of peaks and valleys.

Additionally, and/or alternatively, the foam insert comprises a compressible foam material including a urethane flexible foam or a silicone flexible foam.

DETAILED DESCRIPTION OF THE PREFERRED EMBODIMENTS

Figure 1:
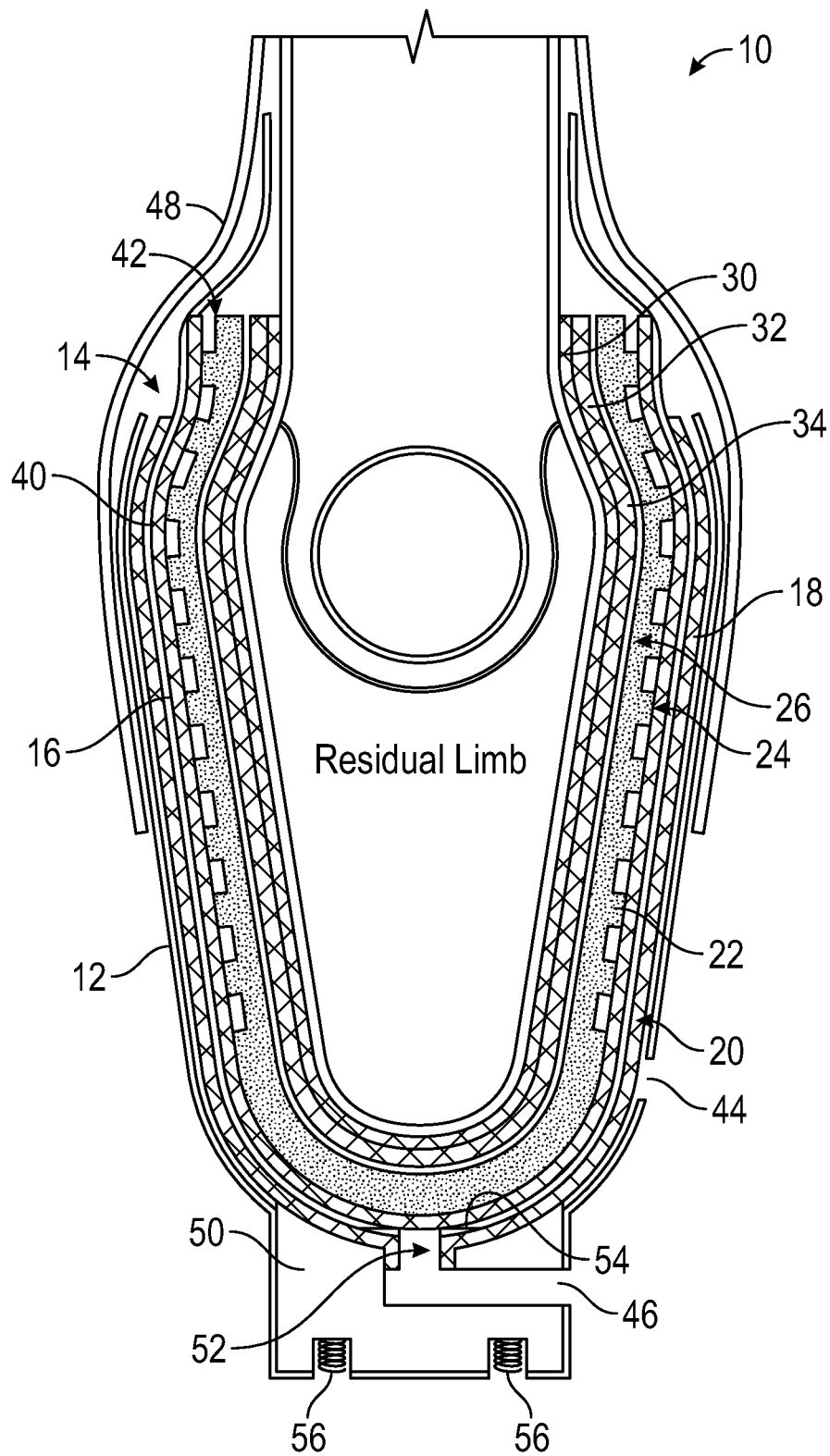
FIG. 1 is a schematic cross-sectional diagram illustrating a walking canister system for manufacturing a prosthetic socket according to an embodiment of the present invention.

The present invention will now be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Those of ordinary skill in the art realize that the following descriptions of the embodiments of the present invention are illustrative and are not intended to be limiting in any way. Other embodiments of the present invention will readily suggest themselves to such skilled persons having the benefit of this disclosure. Like numbers refer to like elements throughout.

In this detailed description of the present invention, a person skilled in the art should note that directional terms, such as "above," "below," "upper," "lower," and other like terms are used for the convenience of the reader in reference to the drawings. Also, a person skilled in the art should notice this description may contain other terminology to convey position, orientation, and direction without departing from the principles of the present invention.

Furthermore, in this detailed description, a person skilled in the art should note that quantitative qualifying terms such as "generally," "substantially," "mostly," and other terms are used, in general, to mean that the referred to object, characteristic, or quality constitutes a majority of the subject of the reference. The meaning of any of these terms is dependent upon the context within which it is used, and the meaning may be expressly modified.

As discussed, prosthetic systems, particularly for lower limbs, include a prosthetic device which is attached to the residual limb via a socket that is custom shaped to the limb. A liner is generally used to adhere the system to the limb and provide a comfortable transfer of the forces applied to the limb. The custom socket is constructed with the aid of a mold that is created from a physical casting or optical scanning of the limb while the limb is relaxed and uninhibited from external stress. The negative casting is transferred to a positive mold and the socket is typically constructed with the application of a fiberglass reinforced thermoplastic layer.

A good fit for the system is determined empirically as the patient wears the prosthetic system over a period of weeks to months. The evaluation criteria include the ability to function, comfort, and consequential sores or tissue damage to the limb based on both clinical and physical evidence. Often the results require that a replacement socket be constructed to adjust the fit.

So, one of the primary issues with fitment which compromises the initial custom shape of the socket is that the limb being measured is not under the normal load which would exist during standing or walking. The compression of the tissue at the distal end and expansion in other areas of the limb are not taken into account. Therefore unusual and non-optimal stresses, both compression and shear may result in discomfort and tissue damage to the limb.

An object of the invention is to provide an approach for measuring the limb for fitment of the socket while the limb is placed under normal load conditions. The challenges may include: 1) the provision for adjustable counter forces on the outer lateral surfaces of the limb to simulate the constraints which would be present with the optimum socket shape while the measurement is being made; 2) the ability to perform precision measurement of the limb without interference from the fitment hardware; and 3) to provide freedom of motion for the patient to move the limb with a stride of walking to better complete the span of measurements for the limb under an extended range of motion.

Additionally, a below-knee (BK) socket manufacture has approximately 13 L codes (the recognized billing code for the healthcare industry). At this time, insurance companies are reducing the amount of reimbursement to O & P facilities for durable medical equipment (DME) by at least 30%. Prosthetics fall under the DME category.

Thus, O & P facilities need to find a more cost-effective way to design and deliver a prosthesis (e.g. below knee prosthesis) than the current industry standard. The average BK prosthesis has at least nine steps. The typical steps may be as follows: measure the patient's residual limb; pour a negative cast to create a positive mold; modify the positive mold to reflect the measurements taken by the practitioner; pull a clear thermoplastic material to create a test socket; set the test socket up on an alignment device with a pylon and foot; walk the patient to determine the fit of the socket and the establish the alignment between the socket and the foot; then, the test socket may be put into an alignment jig and the test socket is re-poured, which maintains the alignment that was established, or if the fit and alignment are unsatisfactory, steps will need to be repeated (unsatisfactory results include, but are not limited to: socket is too loose; socket is too tight; too much friction; any imbalance, etc.); with the positive mold that has maintained alignment, the definitive socket is made by either lamination or thermoplastic; and the socket is assembled with the pylon and the foot, then delivered to the patient, as would be appreciated by those skilled in the art.

With the system, device and method of the present invention, the prosthetic socket may be completed in three steps, instead of the nine steps discussed above. With insurance companies lowering their reimbursements to the provider, and patients paying more out of pocket for their prosthesis, there is a need to lower the cost of the product while also improving the quality of the product.

With the present approach, a more accurate and precise measurement serves the patient as well as the practitioner. A patient must take time off from work for their multiple appointments to the facility. If they rely on a caregiver to transport them, that also creates reduced productivity at a place of employment. An accurate measurement the first time reduces the time spent at the facility. Reduced time at the facility offers the practitioner the ability to see more patients in one work day. This also reduces the materials needed for multiple test sockets. Also, the labor times for technicians per patient is reduced.

Currently, with the above-mentioned current steps, the minimum amount of appointments at the facility is three, with appointment times varying from 30 minutes to 3 hours each time. With the new approach, it is realistic and possible to cast a patient, pour a positive mold, create the test socket, check for fit and alignment, make adjustments and build the definitive prosthetic in the same day, in approximately 3 to 4 hours, for example.

Referring to the cross-sectional view of FIG. 1 and the drawings FIGS. 2-14, the approach including a system, device and method of the present invention is described and illustrated. The example embodiments are best understood from the following detailed description when read with the accompanying drawing figures. Dimensions may be arbitrarily increased or decreased for clarity of discussion.

Referring more specifically to FIGS. 1-6, an example embodiment of a walking canister system 10 (aka ViaWalk™ system) that facilitates the capturing of the shape of a below-knee (BK) residual limb, under load, while the patient is walking, will be described. Using the walking canister system 10, an accurate replication of the boney anatomy and displacement of the soft tissue in a natural orientation may be obtained, leading to a dynamically manufactured prosthetic socket.

The walking canister system 10 includes a rigid canister 12 including an open end 14 at a top, a suspension bladder 16 positioned within the rigid canister 12, and an outer chamber wicking material 18 arranged in an outer chamber 20 defined between the suspension bladder 16 and the rigid canister 12. A foam insert 22 is positioned within the suspension bladder 16 and includes a contoured exterior surface 24 configured to transfer pressure through to an interior surface 26 thereof to produce consistent surface contact with a residual limb, of a walking patient, having casting material thereon. The casting material may typically include a casting sock 30, casting tape 32 (e.g. C-Form casting tape), and an outer casting sock 34, as would be appreciated by those skilled in the art, and as illustrated in FIG. 1, for example.

An inner chamber wicking material 40 is arranged in an inner chamber 42 defined between the foam insert 22 and the suspension bladder 16. An outer chamber vacuum port 44 is positioned in the rigid canister 12 and in fluid communication with the outer chamber 20. An inner chamber vacuum port 46 is positioned in the rigid canister 12 and in fluid communication with the inner chamber 42. An outer chamber suspension sleeve 48 is configured to extend from the residual limb and over the rigid canister 12.

A pylon attachment 50 is located at the bottom of the rigid canister 12 and includes a channel 52 in fluid communication with the inner chamber vacuum port 46. The channel 52 and inner chamber vacuum port 46 may be defined by an interlocking plate 54 at the bottom of the rigid canister 12. Attachment holes 56 (e.g. four threaded attachment holes) are positioned at the bottom of the pylon attachment 50. Other approaches for attaching the rigid canister 12 to a pylon 58 are contemplated as would be appreciated by those skilled in the art. The pylon 58 is attached to the pylon attachment 50, and a floor interface member 60 is positioned at a bottom of the pylon 58 and configured to provide consistent pressure upward through the pylon 58 to the rigid canister 12 during a casting-walking process.

The floor interface member 60 is shown as a large rubber stopper that provides consistent pressure upward through the pylon 58 to the walking canister system 10 during the casting walking process. Other types of floor interfaces may be used, such as a prosthetic foot, as long as the desired consistent pressure is achieved.

Figure 2:
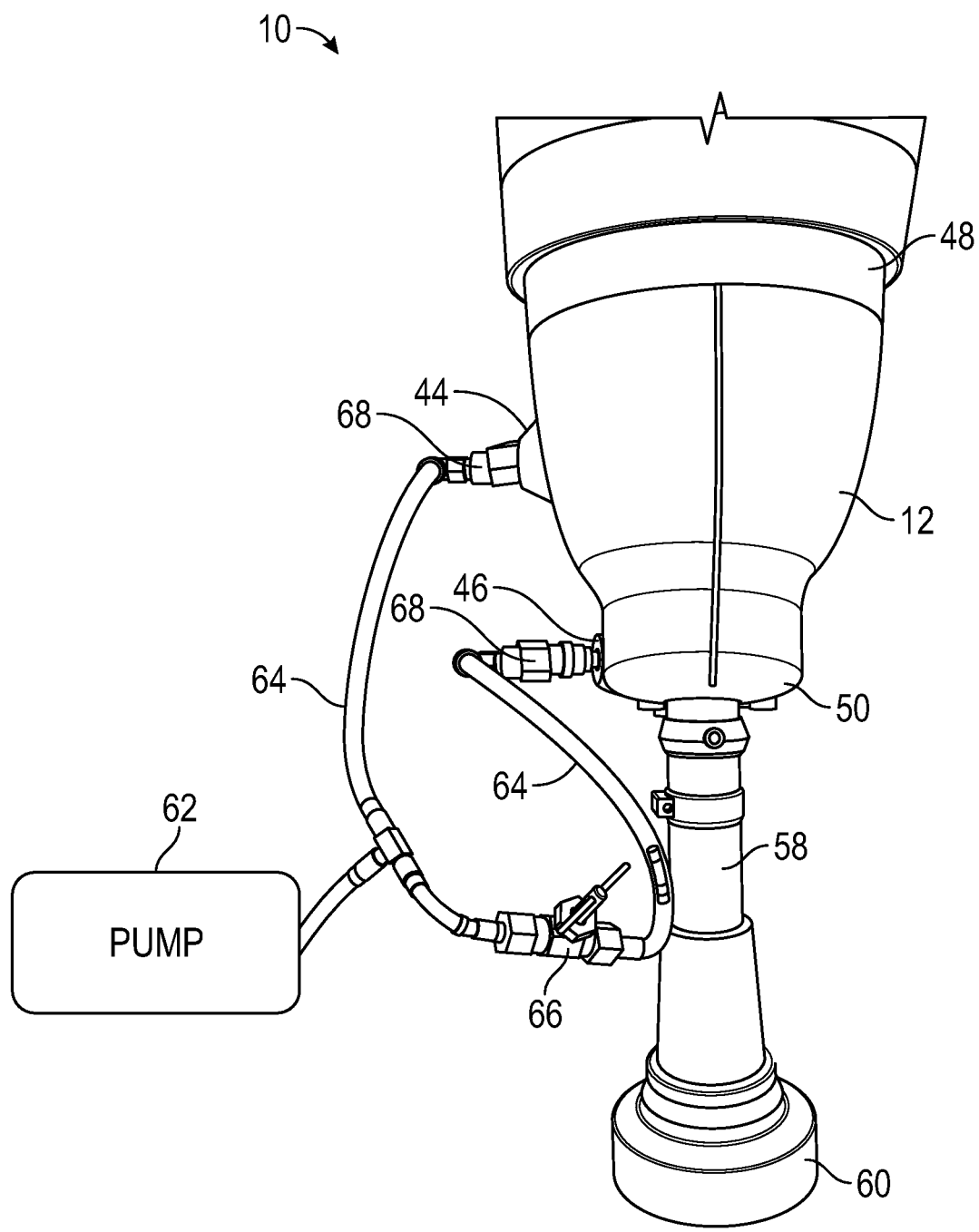
FIG. 2 is a schematic diagram illustrating the lower portion of the walking canister system of FIG. 1 and including the pump, vacuum lines, leg post and floor interface.
Figure 3:
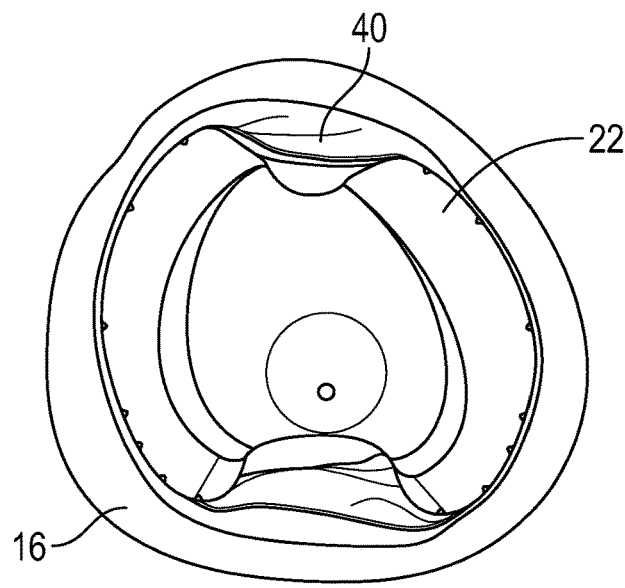
FIG. 3 is a top view of the walking canister system of FIG. 1 with the foam insert, inner chamber wicking material and the suspension bladder (rolled down).
Figure 4:
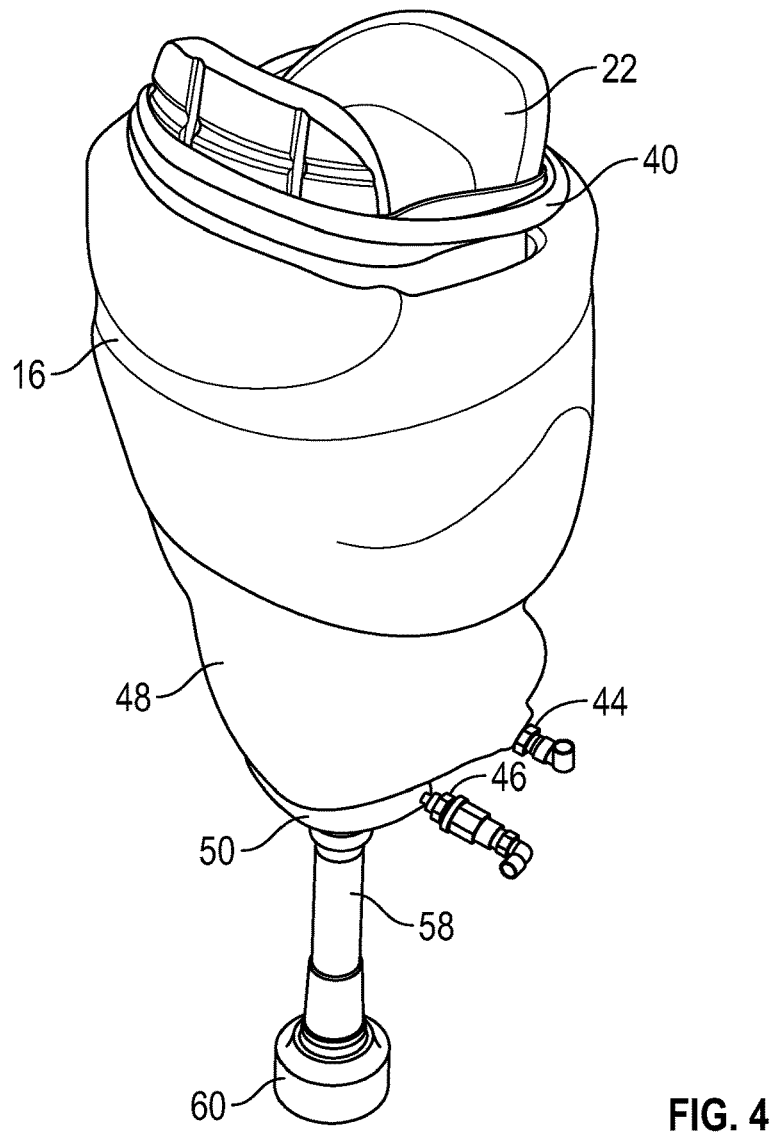
FIG. 4 is a side view of the walking canister system of FIG. 1 mounted on a display platform and with the foam insert, inner chamber wicking material and the rolled down suspension bladder.

As further illustrated in FIG. 2, for example, the walking canister system 10 may include a vacuum or suction pump 62, corresponding tubing 64, valves 66 and couplers 68 to attach to the inner chamber vacuum port 46 and the outer chamber vacuum port 44.

This walking canister system 10 may be set in neutral, with no foot being used, and no other external influence. When the patient walks, the natural alignment (weight line) of the relationship between a prosthetic socket and the foot of the patient may be established, determined, verified and/or defined in conjunction with the prosthetist's know-how and skill.

Figure 5:
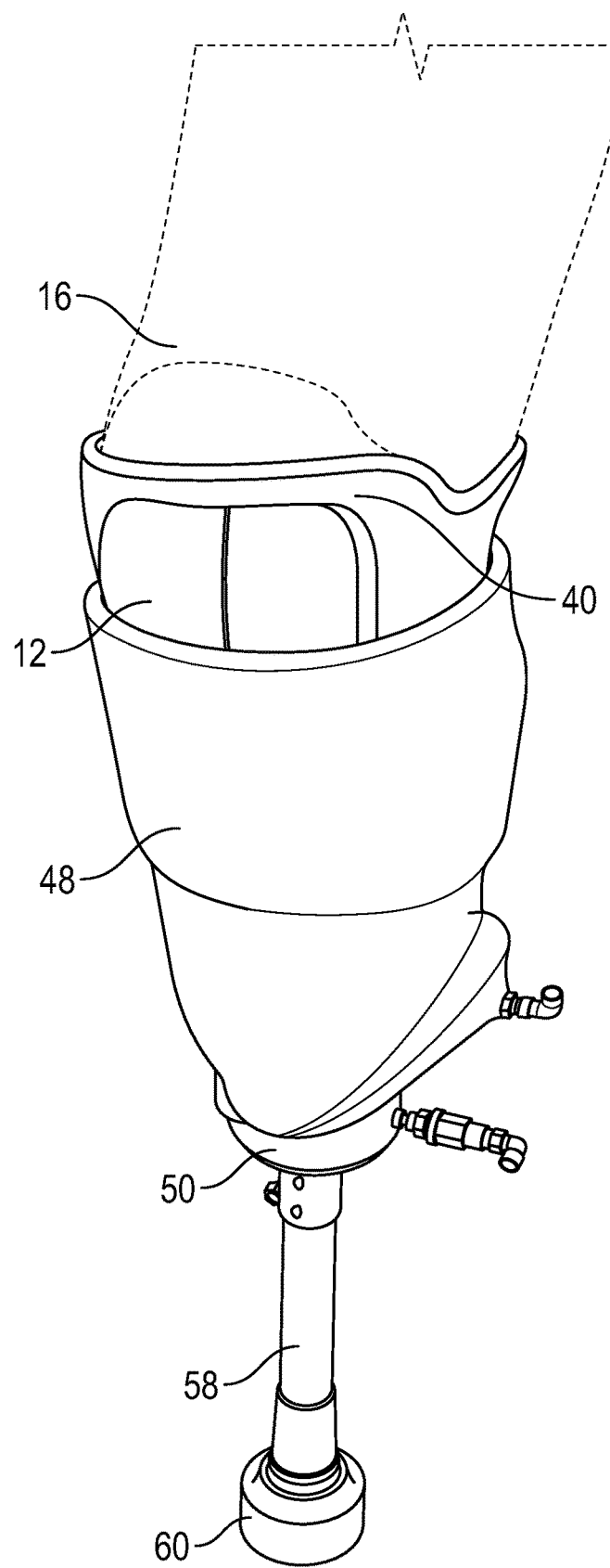
FIG. 5 is a side view of the walking canister system of FIG. 1 illustrating the suspension bladder rolled up, the outer chamber wicking material, a portion of the canister and the outer chamber suspension sleeve (rolled down).
Figure 6:
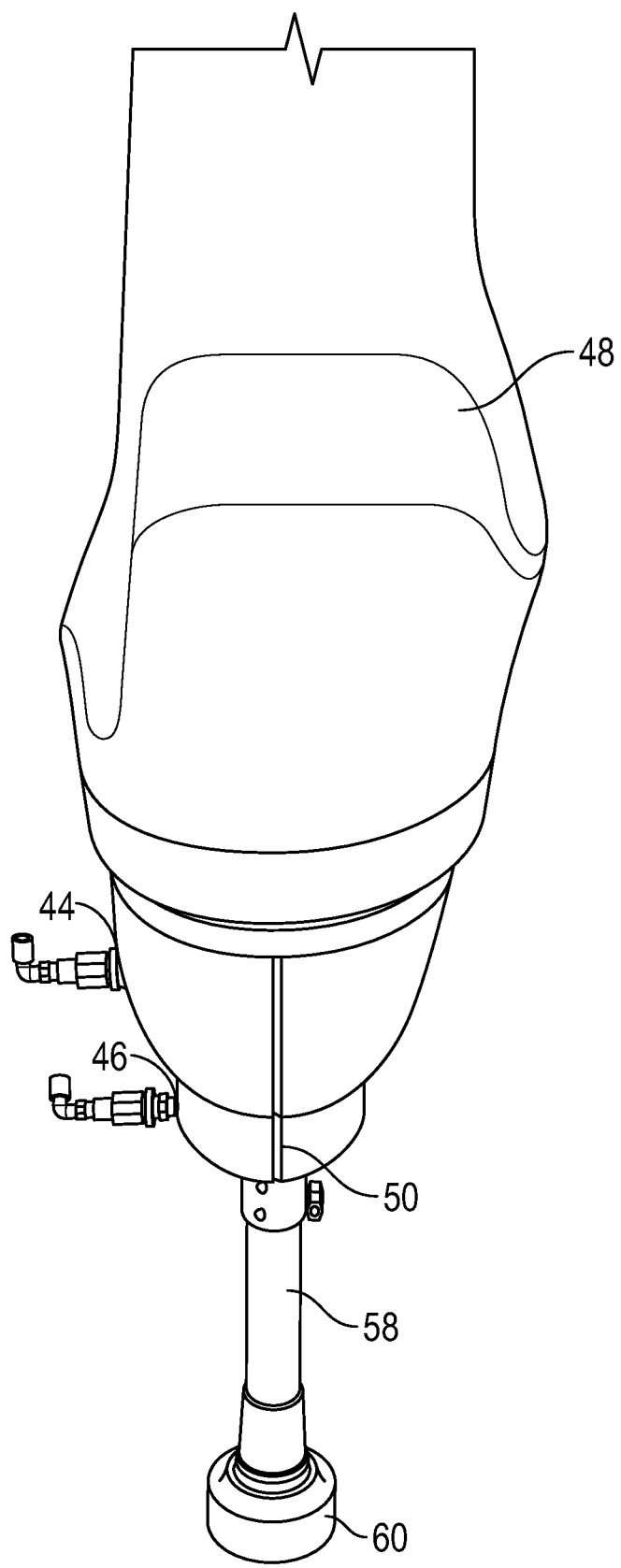
FIG. 6 is a side view of the walking canister system of FIG. 1 illustrating a portion of the canister and the outer chamber suspension sleeve (rolled up).
Figures 7, 8:
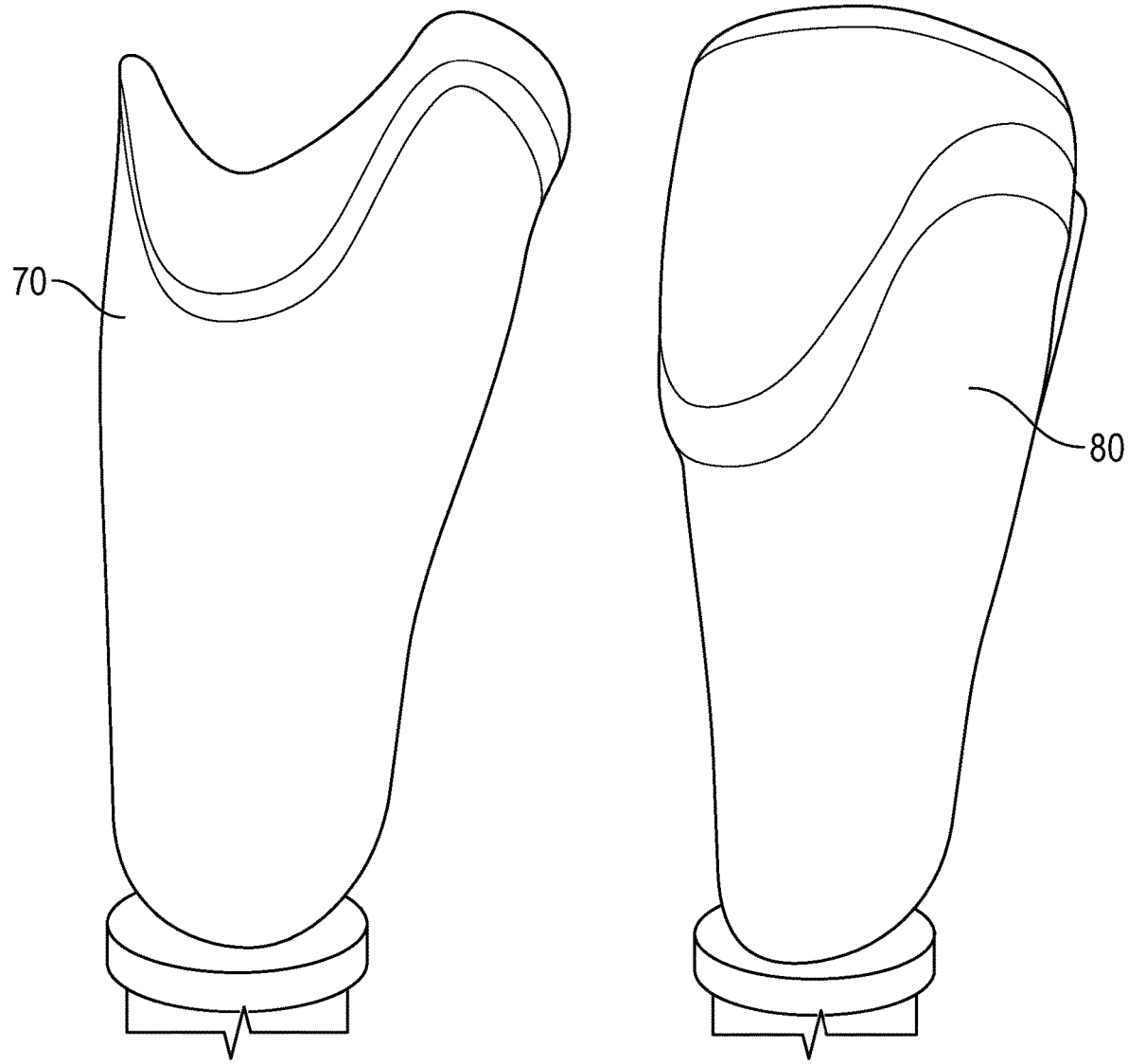
FIG. 7 is a perspective view of an example of a negative cast made with the walking canister system of FIG. 1.
FIG. 8 is a perspective view of an example of a positive mold made from the negative cast of FIG. 7.
Figure 9:
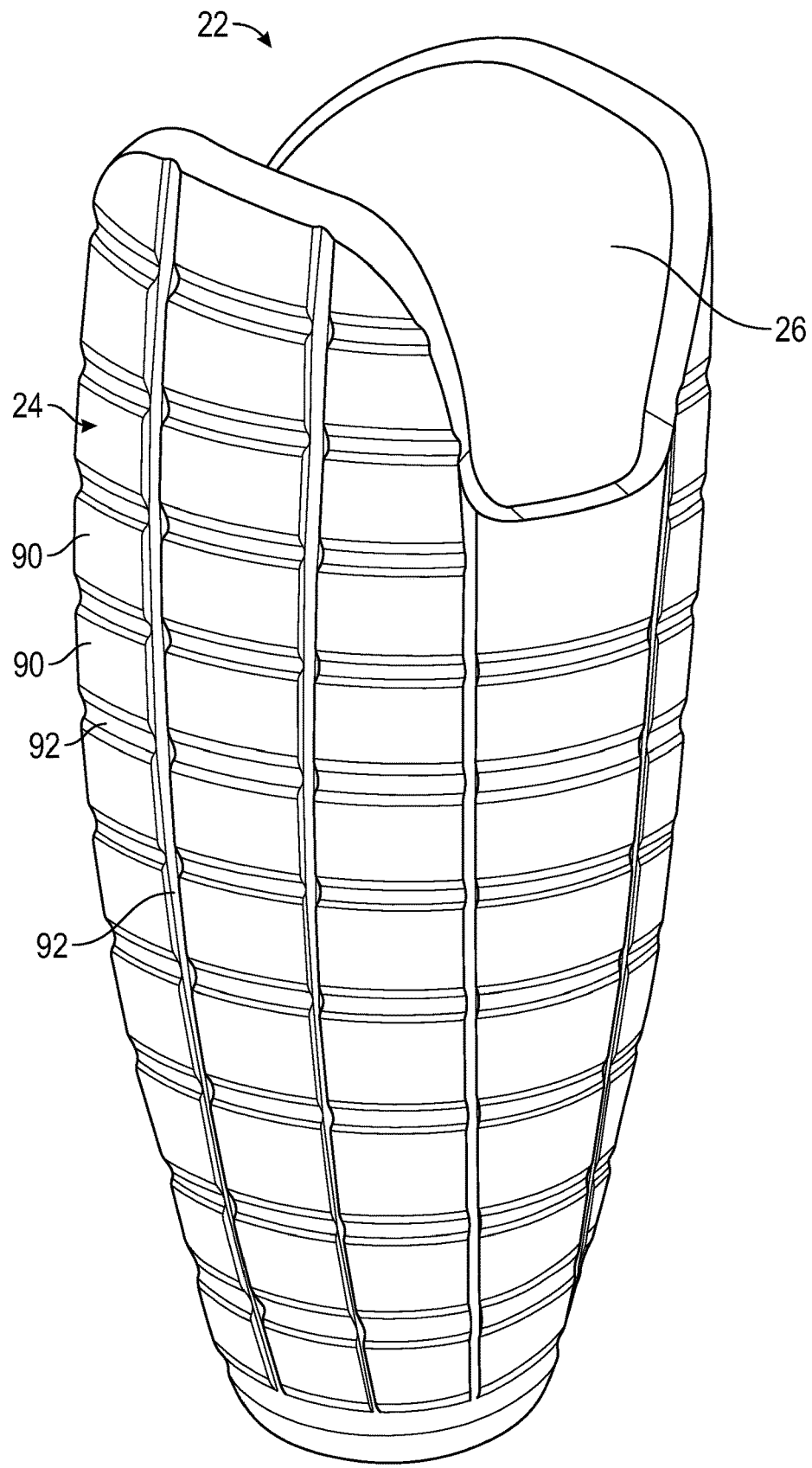
FIG. 9 is a top perspective view of the foam insert for residual limb casting used in the walking canister system of FIG. 1.
Figure 10:
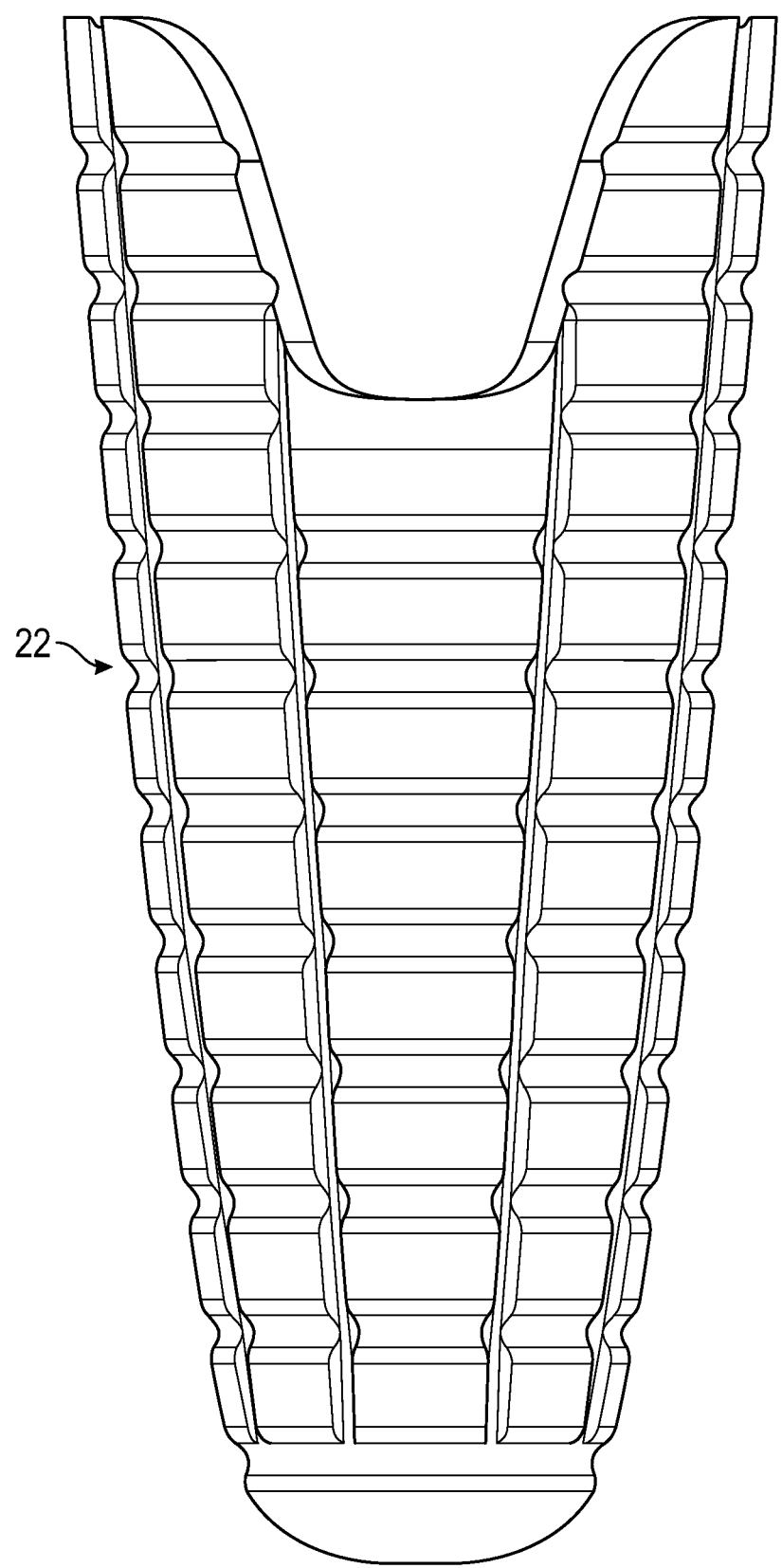
FIG. 10 is a front view of the foam insert for residual limb casting illustrated in FIG. 9.
Figure 11:
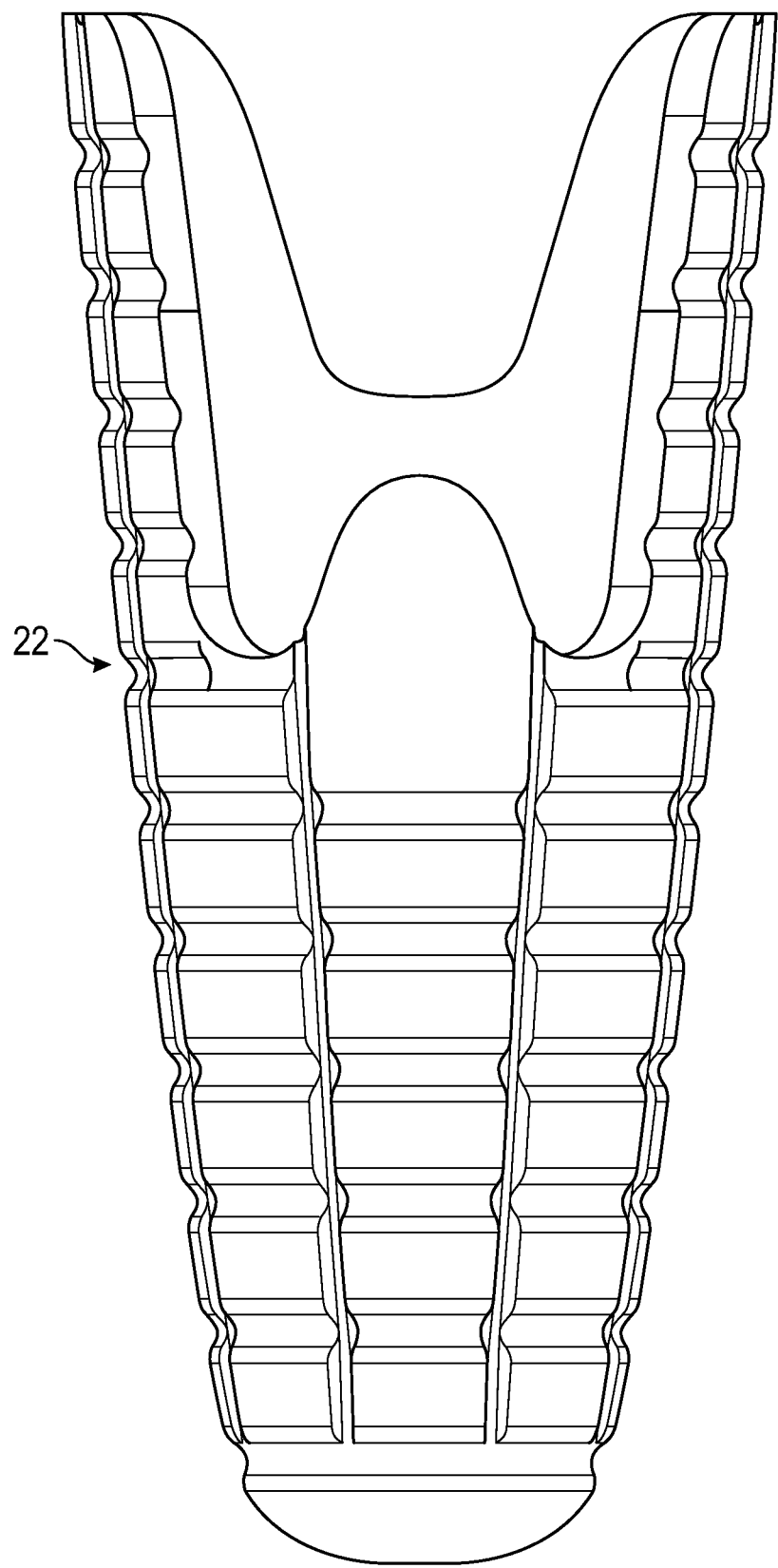
FIG. 11 is a rear view of the foam insert for residual limb casting illustrated in FIG. 9.
Figure 12:
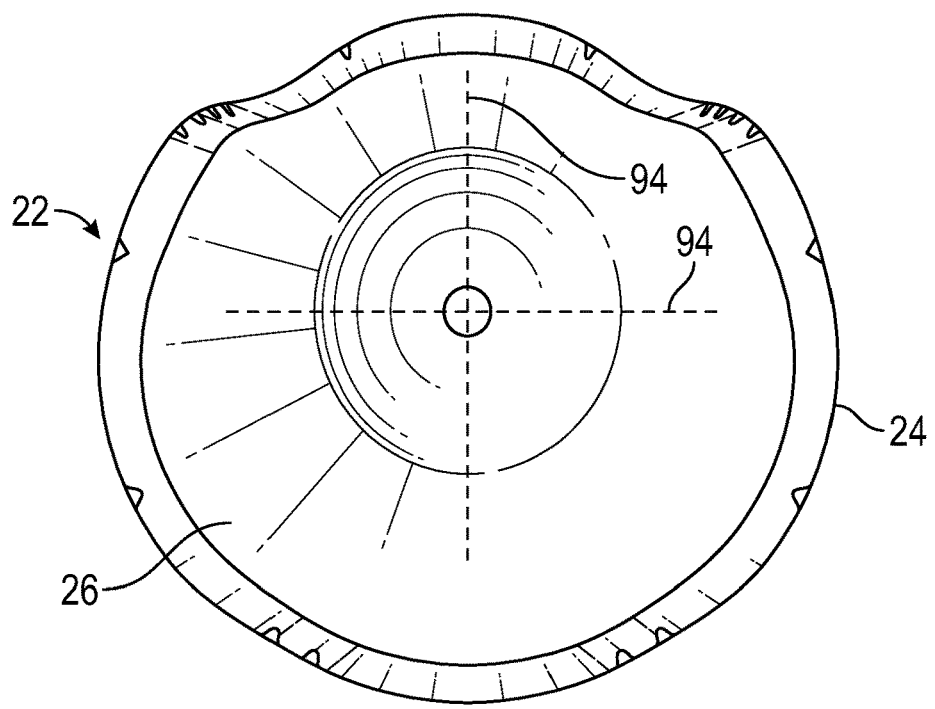
FIG. 12 is a top view of the foam insert for residual limb casting illustrated in FIG. 9.
Figure 13:
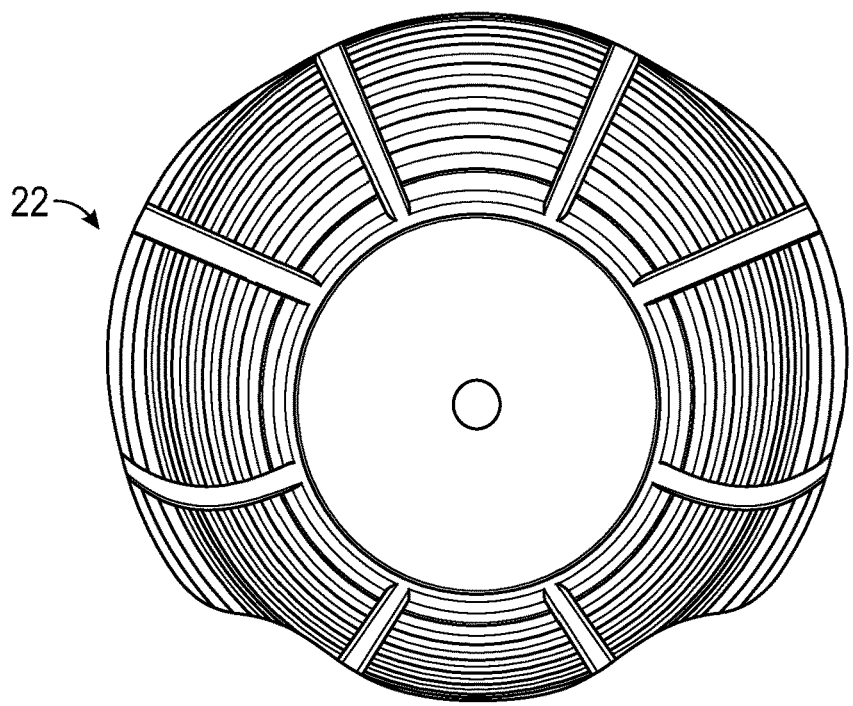
FIG. 13 is a bottom view of the foam insert for residual limb casting illustrated in FIG. 9.
Figure 14:
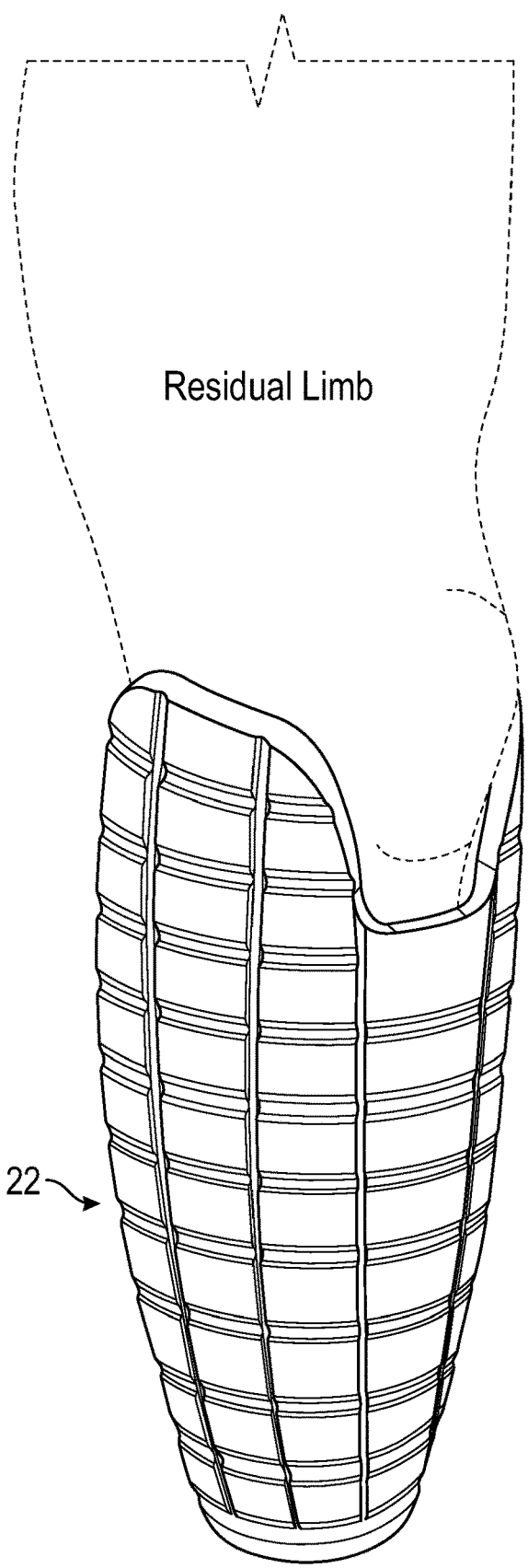
FIG. 14 is another perspective view of the foam insert for residual limb casting of FIG. 9 illustrating the positioning on a residual leg.

The residual limb is casted by using synthetic casting material 30, 32, 34 which is wrapped on the residual limb. Once the casting material is applied, the limb is inserted into the rigid canister 12. The inner vacuum chamber 42 of the rigid canister 12 has the foam insert 22, which is covered with the inner chamber wicking material 40 and the suspension bladder 16 on the outside of the foam insert 22. The suspension bladder 16 is pulled up and over the foam insert 22 to above the knee of the patient (e.g. as illustrated in FIG. 5, for example).

Suction or vacuum is then applied (e.g. in a range of −5 to −15 Hg), which starts the initial suspension and compression in the inner chamber 42 of the foam insert 22. The outer chamber suspension sleeve 48 is rolled up over the foam insert 22 and suspension bladder 16 and it creates a seal above the inner chamber 42. Vacuum is applied to the outer chamber 20 (e.g. in a range of −5 to −15 Hg) and creates additional suction and suspension to prevent any piston action of the limb in the bottom of the inner chamber 42 and rigid canister 12. Thus, the patient is locked in safely and securely to the walking canister system 10, and ready to walk.

The approach is a repeatable process. Multiple users of the walking canister system 10 will obtain the same accurate results. The results are achieved with the present technology and are not dependent on the competency level or experience of the practitioner.

The natural alignment of the patient may vary due to anatomical features of the residual limb. The alignment is determined during the casting process, by transferring alignment reference line(s) within the inner surface 26 of the foam insert 22 onto the outer surface of the casting material sock 34. The alignment relationship between the socket and foot will be reflected on the negative cast 70 (FIG. 7) when it is put onto an alignment holding device prior to forming a positive mold 80 (FIG. 8) therefrom. The negative cast 70 will reflect the relationship between the manufactured socket and foot because the natural angulation of the individual's anatomy in the sagittal and frontal planes is preserved.

Referring additionally to FIGS. 9-14, as illustrated, the foam insert 22 (also referred to as a waffle-cone insert) includes a contoured exterior surface 24 with square or rectangular-shaped peaks 90 and valleys 92 in a matrix configuration. The interior surface 26 is preferably smooth and with application of the vacuum to the chambers, the contoured exterior surface 24 translates and/or transfers pressure through to the interior surface 26 to produce total and/or consistent surface contact with the residual limb via the cast (casting socks 30, 34 and casting tape 32). Other contoured exterior surfaces are contemplated including, for example, a reverse of the pattern shown, or circular peaks and valleys in a matrix, etc., as long as the contoured exterior surface 24 creates pressure through to the interior surface 26 to produce the desired surface contact with the residual limb via the cast. Of course, the waffle-cone insert 22 as shown may aid in the longitudinal and latitudinal orientation of the residual limb and resulting socket fit.

Alignment reference line(s) 94 (FIG. 12) within the inner surface 26 of the foam insert 22 may be transferred onto an outer surface of the casting material sock 34 during the approach for measuring the limb using the walking canister system 10. This may aid in the determination of the natural alignment of the patient during the casting process.

The waffle-cone foam insert 22 is preferably formed using a foam material that is compressible and subsequently expandable. Generally, foam is an object formed by trapping pockets of gas in a liquid or solid. The foam material for the insert 22 should result in the desired properties of translating and/or transferring pressure from the contoured exterior surface 24 through to the interior surface 26 to produce total and/or consistent surface contact with the residual limb via the cast during application of the vacuum to the chambers, as described above. Of course, other materials that achieve this goal are also contemplated.

Solid foams can be closed-cell or open-cell. In closed-cell foam, the gas forms discrete pockets, each completely surrounded by the solid material. In open-cell foam, gas pockets connect to each other. Foams are examples of dispersed media. Foam can also refer to something that is analogous to foam, such as quantum foam, polyurethane foam (foam rubber), XPS foam, polystyrene, phenolic, or many other manufactured foams. Example foam materials may be provided by Smooth-on, Inc. (e.g. FlexFoam-iT!™ series) including mix and pour, high quality urethane and silicone foams that are fast curing and used for industrial, military and art related applications. Foams expand many times original volume. Flexible foams cure flexible and strong.

The rigid canister 12 may be thermoplastic as shown, or any other suitable material that provides the rigidity needed to achieve the results during the walking approach described and shown. The walking canister system 10 may be provided in off-the-shelf sizes (e.g. 7 sizes from smallest to largest) and also in right and left versions.

The present invention may have also been described, at least in part, in terms of one or more embodiments. An embodiment of the present invention is used herein to illustrate the present invention, an aspect thereof, a feature thereof, a concept thereof, and/or an example thereof. A physical embodiment of an apparatus, an article of manufacture, a machine, and/or of a process that embodies the present invention may include one or more of the aspects, features, concepts, examples, etc. described with reference to one or more of the embodiments discussed herein. Further, from figure to figure, the embodiments may incorporate the same or similarly named functions, steps, modules, etc. that may use the same or different reference numbers and, as such, the functions, steps, modules, etc. may be the same or similar functions, steps, modules, etc. or different ones.

The above description provides specific details, such as material types and processing conditions to provide a thorough description of example embodiments. However, a person of ordinary skill in the art would understand that the embodiments may be practiced without using these specific details.

Some of the illustrative aspects of the present invention may be advantageous in solving the problems herein described and other problems not discussed which are discoverable by a skilled artisan. While the above description contains much specificity, these should not be construed as limitations on the scope of any embodiment, but as exemplifications of the presented embodiments thereof. Many other ramifications and variations are possible within the teachings of the various embodiments. While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best or only mode contemplated for carrying out this invention, but that the invention will include all embodiments falling within the scope of the appended claims. Also, in the drawings and the description, there have been disclosed exemplary embodiments of the invention and, although specific terms may have been employed, they are unless otherwise stated used in a generic and descriptive sense only and not for purposes of limitation, the scope of the invention therefore not being so limited. Moreover, the use of the terms first, second, etc. do not denote any order or importance, but rather the terms first, second, etc. are used to distinguish one element from another. Furthermore, the use of the terms a, an, etc. do not denote a limitation of quantity, but rather denote the presence of at least one of the referenced item. Thus, the scope of the invention should be determined by the appended claims and their legal equivalents, and not by the examples given.

Many modifications and other embodiments of the invention will come to the mind of one skilled in the art having the benefit of the teachings presented in the foregoing descriptions and the associated drawings. Therefore, it is to be understood that the invention is not to be limited to the specific embodiments disclosed, and that modifications and embodiments are intended to be included within the scope of the appended claims.

That which is claimed is:

1. A walking canister system for manufacturing a prosthetic socket, the system comprising:
    a rigid canister including an open end at a top;
    a suspension bladder positioned within the rigid canister;
    an outer chamber wicking material arranged in an outer chamber defined between the suspension bladder and the rigid canister;
    a foam insert positioned within the suspension bladder and including a contoured exterior surface configured to transfer pressure through to an interior surface thereof to produce consistent surface contact with a residual limb, of a walking patient, having casting material thereon;
    an inner chamber wicking material arranged in an inner chamber defined between the foam insert and the suspension bladder;
    an outer chamber vacuum port positioned in the rigid canister and in fluid communication with the outer chamber;
    an inner chamber vacuum port positioned in the rigid canister and in fluid communication with the inner chamber; and
    an outer chamber suspension sleeve configured to extend from the residual limb and over the rigid canister.

2. The walking canister system according to claim 1, further comprising a pylon attachment located at the bottom of the rigid canister and including a channel in fluid communication with the inner chamber vacuum port.

3. The walking canister system according to claim 2, wherein the inner chamber vacuum port is defined by an interlocking plate at the bottom of the rigid canister.

4. The walking canister system according to claim 3, further comprising:
    a pylon attached to the pylon attachment; and
    a floor interface member positioned at a bottom of the pylon and configured to provide consistent pressure upward through the pylon to the rigid canister during a casting-walking process.

5. The walking canister system according to claim 1, wherein the rigid canister comprises a thermoplastic rigid canister.

6. The walking canister system according to claim 1, wherein the contoured exterior surface of the foam insert comprises a waffle pattern defining a contoured pattern of squares.

7. The walking canister system according to claim 1, wherein the foam insert comprises a compressible foam material including at least one of urethane and silicon flexible foam.

8. A walking canister method for manufacturing a prosthetic socket, the method comprising:
    providing a rigid canister including an open end at the top;
    positioning a suspension bladder within the rigid canister along with an outer chamber wicking material arranged in an outer chamber defined between the suspension bladder and the rigid canister;
    positioning a foam insert within the suspension bladder and including a contoured exterior surface configured to transfer pressure through to an interior surface thereof to produce consistent surface contact with a residual limb, of a walking patient, having casting material thereon;
    positioning an inner chamber wicking material in an inner chamber defined between the foam insert and the suspension bladder;
    forming an outer chamber vacuum port in the rigid canister and in fluid communication with the outer chamber;
    forming an inner chamber vacuum port in the rigid canister and in fluid communication with the inner chamber; and
    extending an outer chamber suspension sleeve around the top of the rigid canister.

9. The walking canister method according to claim 8, further comprising connecting a pylon attachment at the bottom of the rigid canister and including a channel in fluid communication with the inner chamber vacuum port.

10. The walking canister method according to claim 9, wherein the inner chamber vacuum port is defined by an interlocking plate at the bottom of the rigid canister.

11. The walking canister method according to claim 10, further comprising:
    attaching a pylon to the pylon attachment; and
    positioning a floor interface member at a bottom of the pylon and configured to provide consistent pressure upward through the pylon to the rigid canister during a casting-walking process.

12. The walking canister method according to claim 8, further comprising applying suction to the outer chamber vacuum port and the inner chamber vacuum port to adjust pressure within the outer chamber and the inner chamber.

13. The walking canister method according to claim 8, wherein the contoured exterior surface of the foam insert comprises a waffle pattern defining a contoured pattern of squares.

14. The walking canister method according to claim 8, wherein the foam insert comprises a compressible foam material including at least one of urethane and silicon flexible foam.

* * * * *